US012594365B2

(12) United States Patent
Bai et al.

(10) Patent No.: US 12,594,365 B2
(45) Date of Patent: Apr. 7, 2026

(54) IONIC COMPOUNDS FOR MEDICAL DEVICE APPLICATIONS

(71) Applicant: Becton, Dickinson and Company, Franklin Lakes, NJ (US)

(72) Inventors: He Bai, Sandy, UT (US); James Joseph Semler, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 113 days.

(21) Appl. No.: 18/367,133

(22) Filed: Sep. 12, 2023

(65) Prior Publication Data

US 2024/0139383 A1     May 2, 2024

Related U.S. Application Data

(60) Provisional application No. 63/412,935, filed on Oct. 4, 2022.

(51) Int. Cl.
| | |
|---|---|
| *A61L 2/085* | (2026.01) |
| *A61L 29/08* | (2006.01) |
| *A61L 29/10* | (2006.01) |

(52) U.S. Cl.
CPC ........... *A61L 29/085* (2013.01); *A61L 29/106* (2013.01); *A61L 2300/206* (2013.01); *A61L 2300/404* (2013.01); *A61L 2300/802* (2013.01)

(58) Field of Classification Search
CPC .... A61L 2/085; A61L 2/106; A61L 2300/206; A61L 2300/404; A61L 2300/802
USPC ................................................... 264/211.13
See application file for complete search history.

(56) References Cited

U.S. PATENT DOCUMENTS

| | | | |
|---|---|---|---|
| 3,755,218 | A | 8/1973 | Yen et al. |
| 3,853,804 | A | 12/1974 | Yen et al. |
| 4,642,267 | A | 2/1987 | Creasy et al. |
| 4,664,259 | A | 5/1987 | Landis |
| 4,713,402 | A | 12/1987 | Solomon |
| 5,061,254 | A | 10/1991 | Karakelle et al. |
| 5,147,319 | A | 9/1992 | Ishikawa et al. |
| 5,159,050 | A | 10/1992 | Onwumere |
| 5,322,659 | A | 6/1994 | Walder et al. |

(Continued)

FOREIGN PATENT DOCUMENTS

| | | |
|---|---|---|
| EP | 0184465 B1 | 3/1990 |
| GB | 2 239 604 A | 7/1991 |

(Continued)

OTHER PUBLICATIONS

PCT International Search Report and Written Opinion in PCT/US2023/032829 dated Dec. 5, 2023, 16 pages.

(Continued)

*Primary Examiner* — Christina A Johnson
*Assistant Examiner* — Xue H Liu
(74) *Attorney, Agent, or Firm* — SERVILLA WHITNEY LLC

(57)     ABSTRACT

Medical articles formed from ionically bonding an ionic compound and an active agent provide enhanced properties. The ionic compound comprises an ionic additive incorporated into a base polymer. The ionic additive may be one or more of an anionic additive, a cationic additive, and a zwitterionic additive. Medical articles herein have antimicrobial, anti-fouling, and/or antithrombotic characteristics.

24 Claims, 2 Drawing Sheets

(56) References Cited

U.S. PATENT DOCUMENTS

| | | | |
|---|---|---|---|
| 5,525,348 | A | 6/1996 | Whitbourne et al. |
| 5,693,022 | A | 12/1997 | Haynes |
| 6,261,271 | B1 | 7/2001 | Solomon et al. |
| 6,413,243 | B1 | 7/2002 | Geist |
| 6,866,859 | B2 | 3/2005 | Trogolo et al. |
| 9,314,407 | B2 | 4/2016 | Blizzard et al. |
| 9,561,309 | B2 | 2/2017 | Glauser et al. |
| 9,675,717 | B2 | 6/2017 | Kim et al. |
| 9,895,470 | B2 | 2/2018 | Li et al. |
| 2004/0106912 | A1 | 6/2004 | Rosinskaya et al. |
| 2009/0263431 | A1 | 10/2009 | Fugmann et al. |
| 2013/0216599 | A1 | 8/2013 | Kumar et al. |
| 2015/0151054 | A1 | 6/2015 | Wilkinson |
| 2017/0304815 | A1 | 10/2017 | Vachon et al. |
| 2018/0105665 | A1 | 4/2018 | Day et al. |
| 2020/0269668 | A1 | 8/2020 | Vachon et al. |

FOREIGN PATENT DOCUMENTS

| | | | | |
|---|---|---|---|---|
| WO | WO-2013090808 | A1 * | 6/2013 | ............ G02B 1/043 |
| WO | 2018140911 | A1 | 8/2018 | |
| WO | 2022182971 | A1 | 9/2022 | |
| WO | 2023102436 | A1 | 6/2023 | |

OTHER PUBLICATIONS

PCT International Search Report and Written Opinion in PCT/US2023/032830 dated Dec. 5, 2023, 16 pages.

Edwards Lifesciences Receives FDA Clearance To Market Its Vantex Central Venous Catheter, Edwards Lifesciences, https://www.edwards.com/ns20000621.

Harland Coating Chemistries | Lubricious Hydrophilic Coatings & more, https://harlandmedical.com/products/materials/#antimicrobial-coatings.

Technology—LiquiGlide's permanently wet surface, https://liquiglide.com/tech/.

"A Global Provider of Medical Technologies", Teleflex, https://www.teleflex.com/la/en/product-areas/vascular-access/central-venous-catheters/.

"Astute® Enhanced Lubricious Coating", BioInteractions, https://biointeractions.com/products_astute.php.

"AvertPlus™ Antimicrobial Coating", BioInteractions, https://biointeractions.com/products_avertplus.php.

"Micro Surfaces for Medical Devices", Hoowaki.

"New PICC Mimics Nature", https://www.prweb.com/releases/r4_vascular/biomimetic/prweb2596764.htm.

"Palindrome™ Precision Chronic Hemodialysis Catheters", https://www.medtronic.com/covidien/en-us/products/dialysis-access/chronic-vascular/palindrome-catheters.html.

"The Story of Endexo Anti-Thrombotic Polymer Additives from Interface Biologics", Medical Plastics News, https://www.medicalplasticsnews.com/news/medical-plastics-technology-news/the-story-of-interface-biologics/.

"What is CovaCoat®?", Covalon Technologies Ltd (Http://www.covalon.com).

Begovac, P. C., et al., "Improvements in GORE-TEX1 Vascular Graft Performance by Carmeda1 BioActive Surface Heparin Immobilization", Eur J Vasc Endovasc Surg 25, 432±437 (2003).

Colletta, Alessandro, et al., "S Nitroso N acetylpenicillamine (SNAP) Impregnated Silicone Foley Catheters: A Potential Biomaterial/Device To Prevent Catheter—Associated Urinary Tract Infections", ACS Biomater. Sci. Eng. Jan. 2015, 416-424.

Hazan, Zadik, et al., "Effective Prevention of Microbial Biofilm Formation on Medical Devices by Low-Energy Surface Acoustic Waves", Antimicrobial Agents and Chemotherapy, Dec. 2006, p. 4144-4152, vol. 50, No. 12.

Jamal, Mohamed A., et al., "In Vivo Biocompatibility and In Vitro Efficacy of Antimicrobial Gendine-Coated Central Catheters", Antimicrobial Agents and Chemotherapy, Sep. 2015 vol. 59 No. 9.

Kurt, Pinar, et al., "Highly Effective Contact Antimicrobial Surfaces via Polymer Surface Modifiers", Langmuir 2007, 23, 4719-4723.

Kushwaha, Meenakshi, et al., "A nitric oxide releasing, self assembled peptide amphiphile matrix that mimics native endothelium for coating implantable cardiovascular devices", Biomaterials 31 (2010) 1502-1508.

Liu, Hanyang, et al., "Auranofin Releasing Antibacterial and Antibiofilm Polyurethane Intravascular Catheter Coatings", Frontiers in Cellular and Infection Microbiology, Feb. 2019, vol. 9, Article 37.

Pathak, Rahul, et al., "Inhibition of bacterial attachment and biofilm formation by a novel intravenous catheter material using an in vitro percutaneous catheter insertion model", Medical Devices: Evidence and Research 2018:11 427-432.

Shehatou, Cindy, et al., "Characterizing the Antimicrobial Properties of 405nm Light and the Corning® Light-Diffusing Fiber Delivery System", Lasers in Surgery and Medicine Published by Wiley Periodicals, Inc.

Sotiri, Irini, et al., "Immobilized liquid layers: A new approach to anti-adhesion surfaces for medical applications", Experimental Biology and Medicine 2016; 241: 909-918. DOI: 10.1177/1535370216640942.

Francolini, et al., "Polyurethane anionomers containing metal ions with antimicrobial properties: Thermal, mechanical and biological characterization", Acta Biomaterialia, Elsevier, Amsterdam, NL, vol. 6, No. 9, Sep. 1, 2010 (Sep. 1, 2010), pp. 3482-3490, XP027170162, ISSN: 1742-7061.

Richey, et al., "Surface modification of polyethylene balloon catheters for local drug delivery", Biomaterials, vol. 21, Jan. 1, 2000 (Jan. 1, 2000), pp. 1057-1065.

Sun, Xinbo, "Functional Modification of Biomaterials To Manage Microbial Biofilm Formation", Nov. 4, 2012 (Nov. 4, 2012), pp. 1-193.

* cited by examiner

IONIC COMPOUNDS FOR MEDICAL DEVICE APPLICATIONS

CROSS-REFERENCE TO RELATED APPLICATION

This application claims priority to U.S. Provisional Application No. 63/412,935, filed Oct. 4, 2022, the entire disclosure of which is hereby incorporated by reference herein.

TECHNICAL FIELD

Embodiments of the disclosure generally relate to medical devices and methods of manufacture. More particularly, embodiments of the disclosure are directed to medical devices having an ionic compound ionically bonded to an active agent, the ionic compound comprising an ionic additive incorporated into a base polymer. The active agent may be an antimicrobial agent and/or an antithrombogenic agent.

BACKGROUND

Infusion therapy medical devices, such as syringe cannulas and catheters used for sampling or medicament administration, typically have components that are in direct contact with infusion fluid and/or bodily fluid that can cause infection. For example, catheter-related bloodstream infections may be caused by colonization of microorganisms, which can occur in patients whose treatment includes intravascular catheters and I.V. access devices. These infections can lead to illness and excess medical costs. Impregnating and/or coating catheters and I.V. access devices with various antimicrobial agents (e.g., chlorhexidine, silver, or other antibiotics) is a common approach that has been implemented to prevent these infections.

Some blood contact devices have the potential to generate thrombus. When blood contacts a foreign material, a complex series of events occur. These involve protein deposition, cellular adhesion and aggregation, and activation of blood coagulation schemes. Thrombogenicity has conventionally been counteracted by the use of anticoagulants, such as heparin. Attachment of heparin to otherwise thrombogenic polymeric surfaces may be achieved with various surface coating techniques.

Impregnating catheters and/or I.V. access devices directly with antimicrobial and/or antithrombogenic agents does not create chemical bonding between active agents and polymer substrates, thus devices would lose antimicrobial/antifouling efficacy in a short time.

On the other hand, surface coating techniques are to stabilize (chemically or physically) antimicrobial and/or antithrombogenic agents onto a substrate surface to achieve non-leaching or controlled release of such active agents. However, these coating techniques normally require priming of polymer substrates (e.g., chemical or plasma treatments), followed by multiple surface coating steps, which would complicate the medical device manufacturing process and significantly increase manufacturing costs.

Thus, there is a need for medical devices that can bond and demonstrate controlled release of antimicrobial and/or antithrombogenic agents to achieve antimicrobial and/or anti-fouling characteristics for an extended period of time.

SUMMARY

One or more embodiments are directed a medical device comprising: an ionic compound ionically bonded to an active agent, the ionic compound comprising an ionic additive incorporated into a base polymer.

An additional embodiment is directed to method of manufacturing a medical device, the method comprising: incorporating an ionic additive into a base polymer to form an ionic compound; and ionically bonding the ionic compound and an active agent.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

Figure 1:
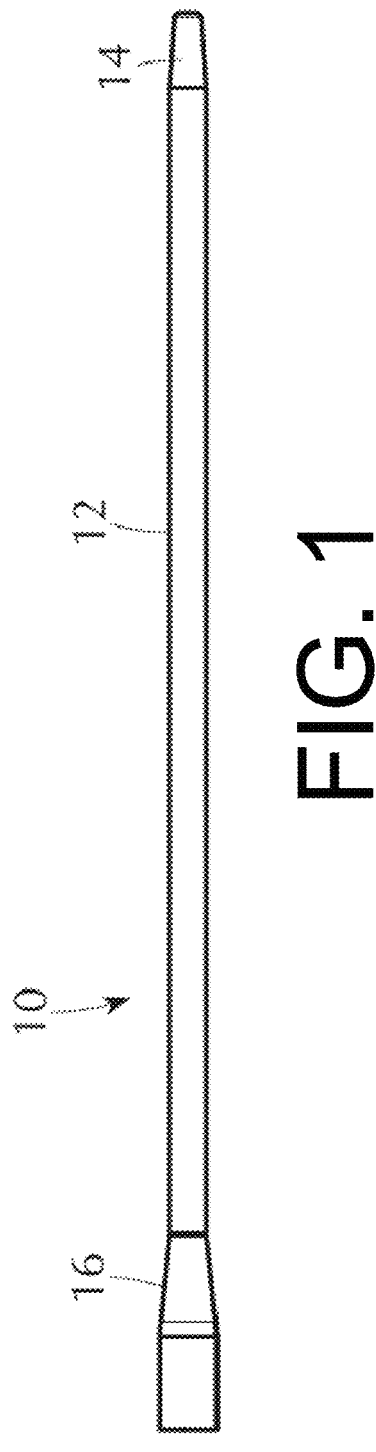
FIG. 1 is a plan view of an exemplary medical device.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

In one or more embodiments, an ionic additive is incorporated into a base polymer to form an ionic compound. The resulting ionic compounds are advantageously used as a binding material for ionic antimicrobial/antithrombogenic agents to achieve controlled release of such ionic agents from medical device components, e.g., catheter, extension, and IV tubing; catheter adapter and luer port; connector body and device housing; and the like.

An ionic additive is an additive containing ionic bonds in its molecular structure. Anionic additives have electronegative groups. Cationic additives have positive charges. Zwitterionic additives have both positive and negative charges in their molecules. The ionic additive does not have the properties of polymers to form a medical device alone, but it may be incorporated into a base polymer to form an ionic compound, and the resulting ionic compound may present the nature of an ionic polymer. An anionic compound (with an anionic additive incorporated into a base polymer) may present the nature of an anionic polymer, which may possess desirable mechanical and/or thermal properties to form a medical device and can also be used as a binding material for cationic antimicrobial/antithrombogenic agents. A cationic compound (with a cationic additive incorporated into a base polymer) may present the nature of a cationic polymer, which may possess desirable mechanical and/or thermal properties to form a medical device and can also be used as a binding material for anionic antimicrobial/antithrombogenic agents. A zwitterionic compound (with both an anionic and a cationic additive or a zwitterionic additive incorporated into a base polymer) may present the nature of a zwitterionic polymer, which may possess desirable mechanical and/or thermal properties to form a medical device and can also be used as a binding material for both cationic and anionic antimicrobial/antithrombogenic agents.

An antimicrobial agent is a substance that kills microorganisms or stops their growth. Antimicrobial agents that can be used for bonding with cationic and/or anionic functional groups of the ionic compound include any anionic antibiotics, e.g., cloxacillin salt, cefoxitin salt, cefazolin salt, penicillin salt, or derivatives thereof, and cationic antiseptics, e.g., chlorhexidine acetate, chlorhexidine gluconate, silver sulfadiazine, benzalkonium chloride, cetylpyridinium chloride, or derivatives thereof. In addition, quaternary ammonium-containing biocides, guanidine-containing biocides, cationic antimicrobial polymers, antimicrobial peptides or peptide-mimics, antifouling phospholipids or phospholipid-mimics, and derivatives thereof can also be ionically bonded with anionic functional groups of the ionic compound to actively and/or passively provide advantages of enhanced surface properties including antimicrobial and/or anti-fouling.

An antithrombogenic agent is a substance which prevents the formation of a blood clot. Anionic antithrombogenic agents, e.g., heparin salt, or derivatives thereof can be ionically bonded with cationic functional groups of the ionic compound to provide antithrombotic properties.

Moreover, the skilled artisan will recognize that anionic and/or cationic biocides and anticoagulants of either small molecules or macromolecules can also be used for bonding with cationic and/or anionic functional groups of the ionic compound.

As used herein, the term "active agent" refers to an antimicrobial agent, an antithrombotic agent, or combinations thereof, which is an anionic, cationic, or zwitterionic molecule that can bind to an ionic compound. Accordingly, in some embodiments, the active agent provides antimicrobial activity, antifouling activity, or a combination thereof.

Principles and embodiments of the present disclosure relate generally to medical devices having improved properties, and methods of preparing and using them. Provided are medical articles, for example, catheter tubing, which have antimicrobial and/or anti-fouling characteristics by ionically bonding and stabilizing active agents to provide desirable material properties, including antimicrobial, antifouling, and/or antithrombogenicity. Provided are ionic compounds that are ionically bonded to antimicrobial/antithrombogenic agents to achieve controlled release of said antimicrobial/antithrombogenic agents from a medical device, e.g., catheter, extensions, IV tubing, catheter adapter, Luer port, connector body, device housing, a component thereof, combinations thereof, and the like, in order to prevent blood stream infections and blood clots, such as deep vein thrombosis (DVT) and thrombosis-induced catheter occlusions.

In FIG. 1, an exemplary medical device in the form of a catheter is illustrated. Tubing made from an ionic compound ionically bonded to an active agent as disclosed herein forms the catheter, which is shaped as needed to receive other components for forming vascular access devices. Catheter 10 comprises a primary conduit 12, which is tubing in its as-extruded form. At a distal end, a tip 14 is formed by a tipping process. At a proximal end, a flange 16 is formed as needed for receipt of other components including but not limited to catheter adapters. Exemplary vascular access devices may include a needle further to the catheter for access to blood vessels.

In one or more embodiments, the medical device is in the form of a catheter, an extension, an IV tubing, a catheter adapter, a luer port, a connector body, a device housing, a component thereof, or a combination thereof. In some embodiments, the catheter comprises a peripherally inserted central catheter (PICC), a peripheral intravenous catheter (PIVC), or a central venous catheter (CVC). In some embodiments, controlled release of the ionically bonded active agent prevents blood stream infections and deep vein thrombosis.

In one or more embodiments, the medical device comprises an ionic compound ionically bonded to an active agent. The ionic compound comprises an ionic additive incorporated into a base polymer. In one or more embodiments, the ionic additive is selected from one or more of a cationic additive, an anionic additive and a zwitterionic additive. In some embodiments, the ionic bond between the active agent and the ionic compound allows non-leaching and/or controlled release of the active agent. In one or more embodiments, the medical device passively reduces thrombus formation and/or bacterial biofilm formation due to ionic repulsion of bacteria, protein, and blood components.

The ionic compound includes one or more cationic and/or anionic functional group. In some embodiments, the anionic compound comprises an anionic functional group. In some embodiments, the anionic compound comprises at least one anionic functional group, at least two anionic functional groups, or at least three anionic functional groups. In some embodiments, the anionic compound comprises more than one anionic functional group, more than two anionic functional groups, or more than three anionic functional groups. In some embodiments, the cationic compound comprises a cationic functional group. In some embodiments, the cationic compound comprises at least one cationic functional group, at least two cationic functional groups, or at least three cationic functional groups. In some embodiments, the cationic compound comprises more than one cationic functional group, more than two cationic functional groups, or more than three cationic functional groups. In some embodiments, the zwitterionic compound comprises an anionic functional group and a cationic functional group. In some embodiments, the zwitterionic compound comprises at least one anionic functional group, at least two anionic functional groups, or at least three anionic functional groups. In some embodiments, the zwitterionic compound comprises at least one cationic functional group, at least two cationic functional groups, or at least three cationic functional groups. In some embodiments, the zwitterionic compound comprises more than one anionic functional group, more than two anionic functional groups, or more than three anionic functional groups. In some embodiments, the zwitterionic compound comprises more than one cationic functional group, more than two cationic functional groups, or more than three cationic functional groups.

In one or more embodiments, the ionic compound is a cationic compound, containing a cationic additive with cationic functional group (e.g., a functional group that has an overall positive charge), which may comprise any suitable cationic functional group known to the skilled artisan. In one or more embodiments, the cationic functional group is selected from one or more of quaternary ammonium ($-N^+$ $(R^1)(R^2)(R^3)$), phosphonium ($-P^+(R^1)(R^2)(R^3)$), imidazolium, pyridinium, sulfonium, guanidinium, thiazolium, and quinolinium, where $R^1$, $R^2$, and $R^3$ independently comprise hydrogen, halogen, alkyl, and aryl.

In one or more embodiments, the ionic compound is an anionic compound, containing an anionic additive with anionic functional group (e.g., a functional group that has an overall negative charge), which may comprise any suitable anionic functional group known to the skilled artisan. In some embodiments, the anionic functional group comprises one or more of carboxylate (—COO⁻), sulfonate (—$SO_3^-$), organosulfate (—O—$SO_3^-$), organophosphate (—O—$PO_3^-$ $R^1$ or (—O—$PO_3^{2-}$), phenolate (—$C_6H_4$—O⁻) and thiolate (—S⁻), where $R^1$ comprises hydrogen, halogen, alkyl, and aryl.

In one or more embodiments, the ionic compound is a zwitterionic compound, containing both an anionic and a cationic additive or a zwitterionic additive with both anionic and cationic functional groups. In some embodiments, the zwitterionic compound comprises two or more functional groups selected from carboxylate (—COO⁻), sulfonate (—$SO_3^-$), organosulfate (—O—$SO_3^-$), organophosphate (—O—$PO_3^-R^1$ or (—O—$PO_3^{2-}$), phenolate (—$C_6H_4$—O—), thiolate (—S⁻), quaternary ammonium (—$N^+(R^1)$ $(R^2)(R^3)$), phosphonium (—$P^+(R^1)(R^2)(R^3)$), imidazolium, pyridinium, sulfonium, guanidinium, thiazolium, and quinolinium, where $R^1$, $R^2$, and $R^3$ independently comprise hydrogen, halogen, alkyl, and aryl.

Ionic additives can be in any suitable form known to the skilled artisan. In one or more embodiments, ionic additives are in a powder form. In other embodiments, ionic additives are in a liquid form.

In one or more specific embodiments, the ionic additive is selected from the group consisting of ionic silica, ionic zeolite, ion-exchange resin, and ionic liquid.

In one or more embodiments, the base polymer can be any suitable base polymer known to the skilled artisan. In some embodiments, the base polymer is an ionic polymer. In other embodiments, the base polymer is nonionic.

Ionic base polymers can comprise any suitable ionic base polymer known to the skilled artisan. In one or more embodiments, the ionic polymer comprises one or more of an anionic polymer, a cationic polymer, and a zwitterionic polymer, wherein the anionic polymer comprises a functional group selected from one or more of carboxylate (—COO⁻), sulfonate (—$SO_3^-$), organosulfate (—O—$SO_3^-$), organophosphate (—O—$PO_3^-R^1$ or (—O—$PO_3^{2-}$), phenolate (—$C_6H_4$—O⁻), and thiolate (—S⁻), wherein the cationic polymer comprises a functional group selected from one or more of quaternary ammonium (—$N^+(R^1)(R^2)(R^3)$), phosphonium (—$P^+(R^1)(R^2)(R^3)$), imidazolium, pyridinium, sulfonium, guanidinium, thiazolium, and quinolinium, wherein the zwitterionic polymer comprises two or more functional groups selected from carboxylate (—COO⁻), sulfonate (—$SO_3^-$), organosulfate (—O—$SO_3^-$), organophosphate (—O—$PO_3^-R^1$ or (—O—$PO_3^{2-}$), phenolate (—$C_6H_4$—O⁻), thiolate (—S⁻), quaternary ammonium (—$N^+(R^1)(R^2)(R^3)$), phosphonium (—$P^+(R^1)$ $(R^2)(R^3)$), imidazolium, pyridinium, sulfonium, guanidinium, thiazolium, and quinolinium, and wherein $R^1$, $R^2$, and $R^3$ independently comprise hydrogen, halogen, alkyl, and aryl.

An ionic base polymer is a polymer which contains both covalent bonds and ionic bonds in its molecular structure. The ionically charged functional group of an ionic base polymer may include one or more of a cationic functional group and an anionic functional group to form one or more of a cationic polymer, an anionic polymer, or a zwitterionic polymer. Cationic polymers are macromolecules that have positive charges, which can be intrinsically present in the polymer backbone and/or in sidechains. Anionic polymers are macromolecules that have electronegative groups, which can be intrinsically present in the polymer backbone and/or in sidechains. Zwitterionic polymers are macromolecules that have both positive and negative charges incorporated into their polymer backbone and/or in sidechains.

Nonionic base polymers can comprise any suitable nonionic base polymer known to the skilled artisan. In one or more embodiments, the nonionic base polymer is selected from one or more of polyurethane, copolyester, polyolefin, polyvinyl chloride, polycarbonate, acrylic-based copolymer, acetal copolymer, cellulose acetate propionate, acrylonitrile butadiene styrene copolymer, high impact polystyrene, thermoplastic elastomer, synthetic rubber, and silicone elastomer, and the like. In one or more specific embodiments, the nonionic base polymer comprises thermoplastic polyurethane (TPU).

In one or more embodiments, the ionic compound is ionically bonded to an active agent. The active agent may be any suitable active agent known to the skilled artisan. In embodiments wherein the ionic compound is an anionic compound, the active agent is a cationic active agent. In embodiments where the ionic compound is a cationic compound, the active agent is an anionic active agent. In embodiments where the ionic compound is a zwitterionic compound, the active agent may be an anionic active agent or a cationic active agent, or both. In one or more embodiments, the active agent is selected from one or more of an anionic active agent and a cationic active agent.

In some embodiments, the cationic active agent may be selected from one or more of chlorhexidine acetate, chlorhexidine gluconate, silver sulfadiazine, benzalkonium chloride, cetylpyridinium chloride, a quaternary ammonium-containing biocide, a guanidine-containing biocide, a cationic antimicrobial polymer, an antimicrobial peptide or peptide-mimics, an antifouling phospholipid or phospholipid-mimics, and derivatives thereof.

In some embodiments, the anionic active agent may be selected from one or more of cloxacillin salt, cefoxitin salt, cefazolin salt, penicillin salt, heparin salt, and derivatives thereof. In addition, the skilled artisan will recognize that anionic and/or cationic biocides and anticoagulants of either small molecules or macromolecules can also be used for bonding with cationic and/or anionic functional groups of the ionic compound.

In one or more embodiments, the medical device releases or is configured to release the active agent in a range of from 4 hours to 90 days. In some embodiments, the medical device releases or is configured to release the active agent over a span of at least 4 hours, at least 8 hours, at least 12 hours, at least 24 hours, at least 48 hours, at least 72 hours, at least 96 hours, at least 120 hours, or at least 144 hours. In some embodiments, the medical device releases or is configured to release the active agent over a span of at least 3 days, at least 7 days, at least 14 days, at least 21 days, at least 30 days, at least 60 days, or at least 90 days.

In one or more embodiments, the ionic additive may be incorporated into the base polymer to form an ionic compound by any suitable means known to the skilled artisan. In some embodiments, the ionic additive may be incorporated into the base polymer by thermally compounding the ionic additive and the base polymer. In some embodiments, the ionic additive may be incorporated into the base polymer by co-dissolving the ionic additive and the base polymer in a suitable solvent system.

In one or more embodiments, a coating including the ionically bonded ionic compound and the active agent is coated on a body of the medical device. In some embodiments, the coating comprises one or more ionic compounds ionically bonded to one or more active agents. In some embodiments, the coating is formed by co-dissolving an ionic compound and an active agent in a solvent system to form an ionic bond between the ionic compound and the active agent. In some embodiments, the solvent system is optimized to prevent damage to the medical device during the coating process. In some embodiments, the solvent system is optimized such that flashing off of solvents after coating of the medical device results in a final surface coating layer with a controlled coating thickness.

The solvent system for the coating may be any suitable solvent system known to the skilled artisan. In one or more embodiments, the solvent system dissolves both the ionic compound and the active agent. In one or more embodiments, the solvent system does not cause damage to the medical device substrate during the coating process. In one or more embodiments, the solvent system may be flashed off after coating. In one or more embodiments, the solvent system includes methyl ethyl ketone, tetrahydrofuran, acetone, ethyl formate, methyl formate, 1,3-dioxolane, ethyl acetate, 2-propanol, ethanol, methanol, or mixtures thereof.

In some embodiments, carriers containing at least one ionic compound can be co-dissolved with at least one active agent in a solvent system to form an ionic bond between the ionic compound and the active agent. In some embodiments, carriers containing at least one ionic compound can be co-dissolved with more than one active agent in a solvent system to form an ionic bond between the ionic compound and the active agent. The coating can then be applied to the surface of the medical device or medical device component.

In some embodiments, the ionic compound can be molded or extruded into medical devices or medical device components, thus, the body of the device includes one or more ionic compounds, and the body of the device is imbibed with one or more active agents. In some embodiments, imbibing may result in loading of the active agent onto the medical device or medical device component by diffusion in addition to ionic bonding.

In one or more embodiments, the medical device comprises a compounded mixture of the ionic compound and the active agent. In some embodiments, the compounded mixture comprises the one or more ionic compounds ionically bonded to the one or more active agents. In one or more embodiments, the compounded mixture can be molded or extruded into medical devices or medical device components.

In one or more embodiments, the medical device comprises at least one excipient. In some embodiments, the at least one excipient is selected from one or more of thermal stabilizers, light stabilizers, anti-blocking agents, antioxidants, antistatic agents, impact modifiers, reinforcing agents, flame retardants, mold release agents, blowing agents, colorants, radiopaque fillers, lubricating agents, and the like. In some embodiments, the medical device may comprise an excipient in an amount in the range of from 0.01 to 50% w/w.

Another aspect of the disclosure relates to methods of manufacturing medical devices. In one or more embodiments, the method comprises incorporating an ionic additive into a base polymer to form an ionic compound; and ionically bonding the ionic compound and an active agent.

In one or more embodiments, incorporating the ionic additive into the base polymer to form an ionic compound can be achieved by any suitable means. Non-limiting examples of suitable techniques include thermally compounding the ionic additive and the base polymer and co-dissolving the ionic additive and the base polymer in a suitable solvent system. In one or more embodiments, the ionic compound comprises the ionic additive in an amount of greater than or equal to: 0.1% w/w, 0.5% w/w, 1% w/w, 1.5% w/w, 2% w/w, 3% w/w, 4% w/w, 5% w/w, 10% w/w, 25% w/w, 50% w/w, 65% w/w, or 80% w/w. In one or more embodiments, the ionic compound comprises the ionic additive in an amount of less than or equal to: 80% w/w, 65% w/w, 50% w/w, 25% w/w, 10% w/w, 8% w/w, 6% w/w, 4% w/w, 2% w/w, or 1% w/w. In one or more embodiments, the ionic compound comprises the ionic additive in an amount ranging from greater than or equal to 0.1 to less than or equal to 80% w/w, and all values and subranges therebetween, including greater than or equal to 0.5 to less than or equal to 65% w/w, greater than or equal to 1 to less than or equal to 50% w/w, and all values and subranges there between; including: greater than or equal to: 0.1% w/w, 0.5% w/w, 1% w/w, 1.5% w/w, 2% w/w, 3% w/w, 4% w/w, 5% w/w, or 10% w/w to less than or equal to: 80% w/w, 65% w/w, 50% w/w, or 25% w/w.

In one or more embodiments, the ionic bonding of the ionic compound and an active agent can be achieved by any suitable technique known in the art. Non-limiting examples of suitable techniques include a bulk mixing technique and an imbibing technique. In some embodiments, the bulk mixing technique comprises a solvent mixing technique and a thermal compounding technique.

In one or more embodiments, the body of the device includes the ionic compound and ionically bonding involves imbibing the body of the medical device with the active agent. In some embodiments, the body of the device also includes the excipient. In one or more embodiments, the body of the device includes the ionic compound in an amount of greater than or equal to: 25% w/w, 50% w/w, 75% w/w, or 100% w/w. In one or more embodiments, the body of the device includes the ionic compound in an amount of less than or equal to: 100% w/w, 75% w/w, or 50% w/w. In one or more embodiments, the body of the device includes the ionic compound in an amount ranging from greater than or equal to 25 to less than or equal to 100% w/w, and all values and subranges therebetween.

In some embodiments, the body of the device includes the ionic compound for bonding of active agents and advantageously does not require priming (e.g., chemical or plasma treatments) of the device. Accordingly, in some embodiments, when the body of the device includes ionic functionalities, the medical device manufacturing process is simplified, and conversion costs are significantly reduced. As used herein, the term "conversion cost" refers to the cost required to load the device with the active agent. In some embodiments, imbibing advantageously provides a medical device where the active agent is ionically bonded on a surface of the medical device and in the body of the device. In one or more embodiments, imbibing provides continuous and long-term supply of the active agent from the device. In one or more embodiments, the medical device comprising the ionic compound is effective to passively reduce thrombus formation and/or bacterial biofilm without imbibing treatment. In one or more embodiments, passive reduction of thrombus formation and/or bacterial biofilm of the ionic compound is due to ionic repulsion of bacteria, protein, and blood components.

In some embodiments, the method further comprises pre-swelling the body of the device. In some embodiments, the method further comprises deionizing the ionic compound. In some embodiments, an ionic bond between the ionic compound and the active agent is formed using the imbibing technique. Accordingly, in some embodiments, the imbibing technique includes deionizing the ionic compound prior to imbibing the body of the device in a solution of the active agent. In some embodiments, the imbibing technique includes pre-swelling the body of the device before deionizing the ionic compound and imbibing the body of the device in a solution of the active agent.

In some embodiments, process parameters for imbibing method may be tuned to optimize loading and elution of the active agent. Accordingly, in some embodiments, the process parameters include process temperatures, process time, a concentration of the active agent, a selection of the solvent system, or combinations thereof.

In some embodiments, ionically bonding the ionic compound and the active agent involves preparing a formulation including the active agent. In some embodiments, the formulation comprises the ionic compound and the active agent. In one or more embodiments, the formulation comprises the ionic compound in an amount of greater than or equal to: 25% w/w, 50% w/w, 75% w/w, or 99.9% w/w. In one or more embodiments, the formulation comprises the ionic compound in an amount of less than or equal to: 99.9% w/w, 75% w/w, or 50% w/w. In one or more embodiments, the formulation comprises the ionic compound in an amount ranging from greater than or equal to 25 to less than or equal to 99.9% w/w, and all values and subranges therebetween.

In one or more embodiments, the formulation comprises the active agent in an amount of greater than or equal to: 0.1% w/w, 0.5% w/w, 1% w/w, 1.5% w/w, 2% w/w, 3% w/w, 4% w/w, 5% w/w, 10% w/w, 25% w/w, 50% w/w, or 75% w/w. In one or more embodiments, the formulation comprises the active agent in an amount of less than or equal to: 75% w/w, 50% w/w, 25% w/w, 10% w/w, 8.0% w/w, 6.0% w/w, 4% w/w, 2% w/w, or 1.0% w/w. In one or more embodiments, the formulation comprises the active agent in an amount ranging from greater than or equal to 0.1 to less than or equal to 75% w/w, and all values and subranges therebetween, including greater than or equal to 0.5 to less than or equal to 50% w/w, greater than or equal to 1 to less than or equal to 25% w/w, and all values and subranges there between; including: greater than or equal to: 0.1% w/w, 0.5% w/w, 1% w/w, 1.5% w/w, 2% w/w, 3% w/w, 4% w/w, or 5% w/w to less than or equal to: 75% w/w, 50% w/w, 25% w/w, 10% w/w, 8.0% w/w, or 6.0% w/w.

In one or more embodiments, preparing the formulation may include thermally compounding the ionic compound and active agent to form an ionically bonded compounded mixture. In one or more embodiments, the compounded mixture comprises the ionic compound in an amount of greater than or equal to: 25% w/w, 50% w/w, 75% w/w, or 99.9% w/w. In one or more embodiments, the compounded mixture comprises the ionic compound in an amount of less than or equal to: 99.9% w/w, 75% w/w, or 50% w/w. In one or more embodiments, the compounded mixture comprises the ionic compound in an amount ranging from greater than or equal to 25 to less than or equal to 99.9% w/w, and all values and subranges therebetween.

In one or more embodiments, the compounded mixture comprises the active agent in an amount of greater than or equal to: 0.1% w/w, 0.5% w/w, 1% w/w, 1.5% w/w, 2% w/w, 3% w/w, 4% w/w, 5% w/w, 10% w/w, 25% w/w, 50% w/w, or 75% w/w. In one or more embodiments, the compounded mixture comprises the active agent in an amount of less than or equal to: 75% w/w, 50% w/w, 25% w/w, 10% w/w, 8.0% w/w, 6.0% w/w, 4% w/w, 2% w/w, or 1.0% w/w. In one or more embodiments, the compounded mixture comprises the active agent in an amount ranging from greater than or equal to 0.1 to less than or equal to 75% w/w, and all values and subranges therebetween, including greater than or equal to 0.5 to less than or equal to 50% w/w, greater than or equal to 1 to less than or equal to 25% w/w, and all values and subranges there between; including: greater than or equal to: 0.1% w/w, 0.5% w/w, 1% w/w, 1.5% w/w, 2% w/w, 3% w/w, 4% w/w, or 5% w/w to less than or equal to: 75% w/w, 50% w/w, 25% w/w, 10% w/w, 8.0% w/w, or 6.0% w/w. In some embodiments, compounding advantageously provides a medical device where the active agent is ionically bonded not only on a surface of the medical device but also in the body of the device, thus resulting in continuous and long-term supply of the active agent from the device.

In some embodiments, compounding of the formulation is processed through a twin-screw compounder. Accordingly, in some embodiments, a ratio of one or more of the ionic compounds, the active agent, and the excipient can be controlled and adjusted by a gravimetric multiple-feeder system. The mixture (conveying through multiple heating and mixing zones) can be continuously passed through a die, a quench tank, and is subsequently cut into regular-sized pellets by a puller-pelletizer. The pellets of the compounded formulation can be used for molding and/or extrusion to form medical devices or medical device components. In some embodiments, the twin-screw compounder process conditions are optimized to achieve uniform mixing of the active agent in the formulation. In some embodiments, uniform mixing is correlated to a desirable elution profile of the active agent from the medical device. In some embodiments, the process parameters of the twin-screw compounder include zone temperatures, screw design, and screw revolutions per minute (RPM). In some embodiments, the method further comprises molding and/or extruding the compounded formulation into the medical device. In some embodiments, the medical device is molded and/or extruded by injection molding and/or extrusion technique.

In one or more embodiments, preparing the formulation may include solvent-mix the ionic compound and active agent, to form an ionically bonded coating formulation. In one or more embodiments, the coating formulation comprises the ionic compound in an amount of greater than or equal to: 25% w/w, 50% w/w, 75% w/w, or 99.9% w/w. In one or more embodiments, the coating formulation comprises the ionic compound in an amount of less than or equal to: 99.9% w/w, 75% w/w, or 50% w/w. In one or more embodiments, the coating formulation comprises the ionic compound in an amount ranging from greater than or equal to 25 to less than or equal to 99.9% w/w, and all values and subranges therebetween.

In one or more embodiments, the coating formulation comprises the active agent in an amount of greater than or equal to: 0.1% w/w, 0.5% w/w, 1% w/w, 1.5% w/w, 2% w/w, 3% w/w, 4% w/w, 5% w/w, 10% w/w, 25% w/w, 50% w/w or 75% w/w. In one or more embodiments, the coating formulation comprises the active agent in an amount of less than or equal to: 75% w/w, 50% w/w, 25% w/w, 10% w/w, 8.0% w/w, 6.0% w/w, 4% w/w, 2% w/w, or 1.0% w/w. In one or more embodiments, the coating formulation comprises the active agent in an amount ranging from greater than or equal to 0.1 to less than or equal to 75% w/w, and all values and subranges therebetween, including greater than or equal to 0.5 to less than or equal to 50% w/w, greater than or equal to 1 to less than or equal to 25% w/w, and all values and subranges there between; including: greater than or equal to:

0.1% w/w, 0.5% w/w, 1% w/w, 1.5% w/w, 2% w/w, 3% w/w, 4% w/w, or 5% w/w to less than or equal to: 75% w/w, 50% w/w, 25% w/w, 10% w/w, 8.0% w/w, or 6.0% w/w.

In some embodiments, the method further comprises applying the coating formulation onto the surface of medical device or medical device component. In some embodiments, such ionically bonded coating formulation advantageously simplifies the medical device manufacturing process and significantly reduces conversion costs. In some embodiments, coating advantageously allows loading of an active agent onto the surface of traditional medical devices.

In some embodiments, process parameters for the coating formulation method may be tuned to optimize loading and elution of the active agent. Accordingly, in some embodiments, the process parameters include process temperatures, process time, ingredient concentrations, a selection of the solvent system, or combinations thereof.

EXAMPLES

Example 1

Preparation of Ionic Compounds

Three ionic additives, as shown in Table 1, were used for preparation of ionic compounds:

TABLE 1

| | Ionic Additive | Structure | Physical Form | Ion Exchange Capacity (mmol/g) |
|---|---|---|---|---|
| A | Tosic Acid (Sodium Salt Form) Grafting on Silica (SCX-Na) | Silica—⟨⟩—SO$_3^-$Na$^+$ | Powder | 0.51 |
| B | Propyl Sulfonic Acid (Sodium Salt Form) Grafting on Silica (SCX-2-Na) | Silica—SO$_3^-$Na$^+$ | Powder | 0.62 |
| C | Ion-Exchange Resin (C100MRNS) | Copolymer of Styrene Crosslinked with Divinylbenzene, Sulfonic Acid, Sodium Salt From | Powder | 3.10 |

The base polymer (nonionic) used in this work was a thermoplastic polyurethane (TPU), which is the reaction product of a diisocyanate, a polyglycol, and a diol chain extender.

Each ionic additive (A-C) was compounded with the base polymer using a twin-screw compounder to form a corresponding ionic compound. During compounding, granulates of base polymers as well as powders of ionic additives were fed into a twin-screw compounder simultaneously. The mix ratio was controlled and adjusted by a gravimetric multiple-feeder system. Ionic additives do not melt and the powders are uniformly mixed into base polymer melts during the twin-screw thermal compounding process. The mix (conveying through multiple heating zones) continuously passed through a die, a quench tank, and was subsequently cut into regular-sized pellets by a puller-pelletizer.

Table 2 shows the compositions of the ionic compounds prepared in this work

TABLE 2

| Ionic Compound | Composition |
|---|---|
| SC-1 | 90 wt. % base polymer TPU/10 wt. % A |
| SC-2 | 90 wt. % base polymer TPU/10 wt. % B |
| SC-3 | 90 wt. % base polymer TPU/10 wt. % C |
| Reference | Base polymer TPU without ionic additives |

Example 2

Testing

Calculation of Ion Exchange Capacity. The ion exchange capacity (mmol/g) of ionic compounds can be easily calculated based on their compositions as shown in Table 3.

TABLE 3

| Ionic Compound | Ion Exchange Capacity (mmol/g) |
|---|---|
| SC-1 | 0.051 |
| SC-2 | 0.062 |

TABLE 3-continued

| Ionic Compound | Ion Exchange Capacity (mmol/g) |
|---|---|
| SC-3 | 0.310 |
| Reference | 0 |

The pellets of ionic compounds in Table 2 were subsequently extruded into ribbon sheets for material physical property characterizations. The thickness of the ribbon sheets was 0.007-0.010 in.

Tensile Property Testing. Tensile properties of both the reference base TPU polymer and the ionic compound ribbons (thickness of 0.007-0.010 in.) were characterized using Instron. The testing was performed at standard room condition (23° C., 50% RH, and >40 h equilibration time), which is provided in Table 4 (mean of 10 measurements for each data).

TABLE 4

| Example | Tensile at break (psi) — Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) |
|---|---|---|---|---|---|---|---|
| SC-1 | 7848.02 — 340.27 | 674.18 | 1442.07 | 1957.72 | 2930.70 | 4404.36 | 123.09 |
| SC-2 | 4401.42 — 305.16 | 534.90 | 1144.38 | 1522.52 | 2201.15 | 3094.63 | 96.46 |
| SC-3 | 3299.83 — 265.83 | 424.01 | 896.51 | 1120.54 | 1512.41 | 2596.74 | 75.48 |
| Reference | 11778.56 — 395.61 | 574.37 | 1257.72 | 1720.20 | 2607.27 | 4754.87 | 100.47 |

Testing was also performed at body indwell conditions (37° C., saline solution equilibration for 4 hours), which is provided in Table 5 (mean of 10 measurements for each data). Soften ratio is defined according to the following Equation (1).

$$\text{Soften Ratio} = \frac{\text{Young's Modulus at Room Conditions} - \text{Young's Modulus at Body Indwell Conditions}}{\text{Young's Modulus at Room Conditions}} \times 100\% \qquad \text{Equation (1)}$$

Water Sorption. The reference base TPU polymer and the ionic compound ribbons went through the following procedures for water sorption measurements: (i) cut ribbons (5 replicates for each group of ribbon material) into rectangular shape; (ii) dried all sample ribbon cuts in a vacuum oven at 95° C. overnight; (iii) weighed each dry ribbon cut; (iv) submerged each dry ribbon cut into 37° C. de-ionized water for 4 h; (v) immediately after taking the ribbon cut out of water, used a tissue paper to wipe off the surface free water and re-weighed the saturated ribbon cut; (vi) recorded all the pre-hydration and post-hydration weight data and calculated water sorption based on the following Equation (2).

TABLE 5

| Example | Tensile at break (psi) — Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) | Soften Ratio (%) |
|---|---|---|---|---|---|---|---|---|
| SC-1 | 6733.74 — 477.22 | 288.48 | 749.09 | 888.45 | 1201.07 | 2043.62 | 43.41 | 64.73 |
| SC-2 | 3459.70 — 403.93 | 289.94 | 693.23 | 807.86 | 1058.59 | 1606.10 | 45.03 | 53.32 |
| SC-3 | 2862.43 — 394.50 | 181.08 | 458.83 | 536.49 | 645.15 | 1125.44 | 27.59 | 63.45 |
| Reference | 9766.69 — 501.52 | 233.63 | 661.50 | 806.82 | 994.61 | 1963.63 | 34.43 | 65.73 |

Data in Tables 4 & 5 show that with introduction of ionic additives A-C in powder form compounding into base TPU polymer, the resulting ionic compounds SC-1, SC-2 and SC-3 all showed reduced mechanical properties (ultimate tensile strength and ultimate tensile strain) both at room and at simulated body indwell conditions, since the ionic additives do not contribute to material mechanical strength. Ionic compound SC-1 showed the least mechanical property drop compared to the base TPU polymer. Even with reduction of material mechanical strength after compounding, the resulting ionic compounds still have great potential to be used for various medical device applications, including catheter tubing materials. In addition, these ionic compounds showed comparable material stiffness (Young's modulus) both at room and at simulated body indwell conditions compared to the base TPU polymer, resulting in comparable material soften ratio.

$$\text{Water Sorption} = \frac{\text{Post Hydration Sample Weight} - \text{Dry Sample } Weigth}{\text{Dry Sample } Weigth} \times 100\% \qquad \text{Equation (2)}$$

Table 6 shows the water sorption data (mean of 5 measurements for each data).

TABLE 6

| Example | Water Sorption (%) |
|---|---|
| SC-1 | 2.53 |
| SC-2 | 2.35 |

TABLE 6-continued

| Example | Water Sorption (%) |
|---------|-------------------|
| SC-3 | 10.58 |
| Reference | 1.80 |

Data in Table 6 show that introduction of ionic (sulfonate) functional group resulted in increased material water sorption due to hydrophilic nature of sulfonate functionalities. Ionic compounds SC-1 and SC-2 have low ionic content, thus slightly increased water sorption compared to the base TPU polymer; ionic compound SC-3 has higher ionic content, thus more significant increase of water sorption.

Hydratability. The reference base TPU polymer and the ionic compound ribbons went through the following procedures for hydratability measurements: (i) cut ribbons (5 replicates for each group of ribbon material) into rectangular shape; (ii) measured the dimensions (length and width) of each ribbon cut; (iii) submerged each ribbon cut into 37° C. saline solution for 4 h; (iv) immediately after taking the ribbon cut out of saline solution, re-measured the dimensions (length and width) of each saturated ribbon cut; (v) recorded all the pre-hydration and post-hydration dimension data and calculated dimensional change based on the following Equation (3).

$$\text{Dimensional Change} = \frac{\text{Post Hydration Sample Dimension} - \text{Original Sample Dimension}}{\text{Original Sample Dimension}} \times 100\% \quad \text{Equation (3)}$$

Table 7 shows the hydratability data (mean of 5 measurements for each data).

TABLE 7

| Example | Dimensional Change - Length (%) | Dimensional Change - Width (%) |
|---------|-------------------------------|-------------------------------|
| SC-1 | 0.61 | 0.65 |
| SC-2 | 0.47 | 0.64 |
| SC-3 | 2.56 | 2.95 |
| Reference | 0.49 | 0.45 |

Data in Table 7 show that material hydratability correlates to water sorption. Ionic compounds SC-1 and SC-2 only had slight increase of water sorption compared to the reference base TPU polymer, thus showed comparable dimensional changes after hydration; however, ionic compound SC-3 had significantly higher water sorption, thus showed higher dimensional changes after hydration.

Water Extraction. The ionic compound ribbons went through the following procedures for water extraction measurements: (i) cut ribbons (5 replicates for each group of ribbon material) into rectangular shape; (ii) dried all sample ribbon cuts in a vacuum oven at 95° C. overnight; (iii) weighed each dry ribbon cut; (iv) submerged each ribbon cut into 37° C. de-ionized water for 4 h; (v) after soaking, each sample ribbon cut was dried again in a vacuum oven at 95° C. overnight, then re-weighted each dry ribbon cut; (v) recorded all the pre-soaking and post-soaking dry weight data and calculated Extraction Loss based on the following Equation (4).

$$\text{Extraction Loss} = \frac{\text{Sample Dry Weight prior Soaking} - \text{Sample Dry Weight Prior Soaking}}{\text{Sample Dry Weight Prior Soaking}} \times 100\% \quad \text{Equation (4)}$$

Table 8 shows the extraction loss data (mean of 5 measurements for each data) for ionic compounds SC-1, SC-2, and SC-3.

TABLE 8

| Ionic Compound | Extraction Loss (%) |
|----------------|---------------------|
| SC-1 | 0.0174 |
| SC-2 | 0.0286 |
| SC-3 | −0.0647 |

Data in Table 8 show that the extraction weight loss after 37° C. water soaking is negligible; All three ionic compounds are stable and there are negligible leach out of the ionic additives.

Ionic Bonding and Elution of Cationic Antimicrobial Agent. The ionic compounds SC-1, SC-2 and SC-3 ribbons were used as the substrates and chlorhexidine acetate was used as the cationic antimicrobial agent for bonding and elution studies.

Imbibing Coupon (Condition A): ribbon sheets (thickness of 0.007-0.010 in.) of the ionic compounds SC-1 and SC-3 were cut into rectangularly shaped coupons (rectangular area of ~5 cm$^2$); the coupons were soaked in 10 mL of chlorhexidine acetate (100 mM)/sodium citrate (1 mM) solution in 30/70 v/v% of methanol/water at 37° C. for 24 hours for loading of cationic antimicrobial agent; coupons were placed on an Orbital Shaker during this loading process; after loading, the coupons were soaked in 10 mL of methanol for 1 minute at room temperature to rinse off the loading solution; finally, the coupons were dried in a fume hood at room temperature overnight to flash off residue methanol solvent. The resulting imbibed couples are named SC-1-A and SC-3-A.

Imbibing Coupon (Condition B): ribbon sheets (thickness of 0.007-0.010 in.) of the ionic compounds SC-1, SC-2, and SC-3 were cut into rectangularly shaped coupons (rectangular area of ~5 cm$^2$); the coupons were soaked in 10 mL of 400 mM of chlorhexidine acetate in methanol solution at 37° C. for 24 hours for loading of cationic antimicrobial agent; coupons were placed on an Orbital Shaker during this loading process; after loading, the coupons were soaked in 10 mL of methanol for 1 minute at room temperature to rinse off the loading solution; finally, the coupons were dried in a fume hood at room temperature overnight to flash off residue methanol solvent. The resulting imbibed couples are named SC-1-B, SC-2-B, and SC-3-B.

Chlorhexidine Elution in Human or Bovine Serum: the coupons loaded with chlorhexidine, as described above (SC-1-A, SC-3-A, SC-1-B, SC-2-B and SC-3-B), were soaked in the elution media comprising 60/40 v/v% of human (or bovine) serum/phosphate buffered saline at 37° C. (on Orbital Shaker@150 RPM) for time intervals of 3 h, 6 h, 24 h, 48 h, 72 h, 96 h, and 168 h. At each designated time interval, the previous elution media was removed for chlorhexidine elution analysis and quantification by high-performance liquid chromatography (HPLC) and fresh elution media was used for the next time interval. Chlorhexidine elution is defined as the mass of chlorhexidine (in terms of chlorhexidine acetate equivalence) eluted from the coupon per unit area of coupon sample in the unit of µg/cm$^2$.

Chlorhexidine Post-Elution Extraction: after 7 days of human (or bovine) serum elution testing, the remaining chlorhexidine in each coupon was completely extracted using the extraction media comprising 0.3/70/30 v/v/v% of trifluoroacetic acid/acetonitrile/water at 37° C. for 24 hours (on Orbital Shaker@150 RPM), followed by analysis and quantification of remaining chlorhexidine in each coupon by HPLC; The chlorhexidine remain is defined as the mass of chlorhexidine (in terms of chlorhexidine acetate equivalence) remained in the coupon per unit area of coupon sample in the unit of $\mu g/cm^2$.

Chlorhexidine Loading Calculation: chlorhexidine initial loading on the coupon can be calculated by adding total chlorhexidine human (or bovine) serum elution (adding up all elution time points) and the chlorhexidine remain (by post-elution extraction).

Table 9 shows the chlorhexidine initial loading data (average of 3 replicates) of the ionic compounds SC-1, SC-2, and SC-3 at imbibing Condition A and Condition B.

TABLE 9

| Example | Chlorhexidine Initial Loading ($\mu g/cm^2$) |
|---|---|
| SC-1-A | 154.2 |
| SC-1-B | 295.1 |
| SC-2-B | 556.9 |
| SC-3-A | 248.8 |
| SC-3-B | 305.0 |

Chlorhexidine loading data in Table 9 show that even though these ionic compounds have low ionic content (ion exchange capacity), they still exhibited decent chlorhexidine loading after imbibing, which is much higher than materials without ionic functionalities (only ~50 $\mu g/cm^2$); we are expecting much higher chlorhexidine loading after further increasing the ionic content of such ionic compounds. In addition, imbibing Condition B (400 mM of chlorhexidine acetate in methanol solution) resulted in higher chlorhexidine loading than imbibing Condition A. Moreover, ionic compounds SC-1 and SC-2 have much lower ionic content (ion exchange capacity), but comparable or higher chlorhexidine loading compared to ionic compound SC-3, which indicates that ionic additives A and B (ionic silica) might be more preferrable for this application. Ionic compound SC-2 (using ionic additive B) shows the highest chlorhexidine loading among the three.

Table 10 shows the chlorhexidine elution in human or bovine serum and chlorhexidine remain data (average of 3 replicates) of the imbibed ionic compounds SC-1-A, SC-1-B, SC-2-B, SC-3-A and SC-3-B.

Figure 2:
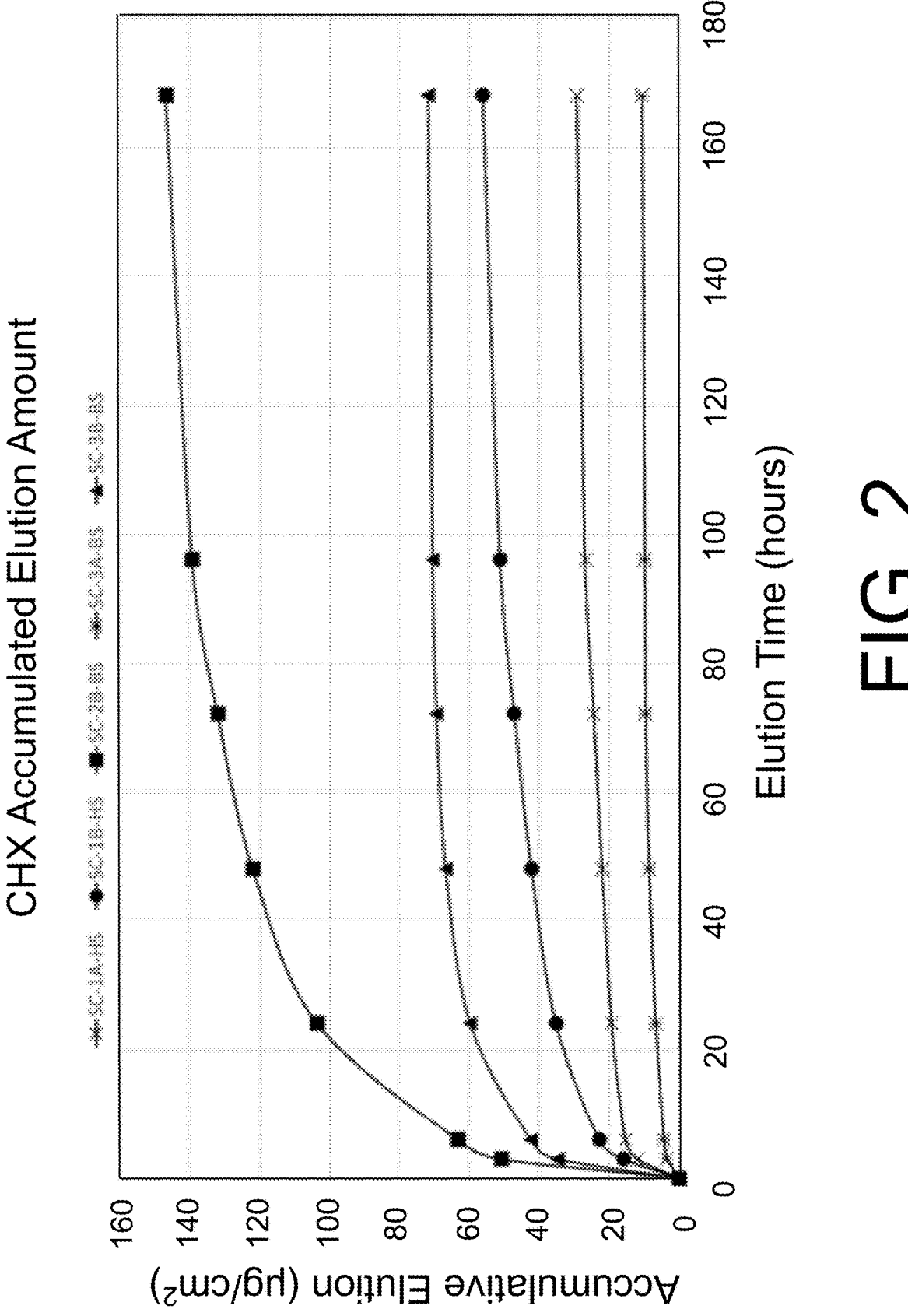
FIG. 2 illustrates an elution profile of a medical device according to one or more embodiments of the disclosure.

FIG. 2 shows the accumulated chlorhexidine elution in human or bovine serum over a period of time (7 days) for the imbibed ionic compounds SC-1-A, SC-1-B, SC-2-B, SC-3-A and SC-3-B.

SC-2-B has the highest chlorhexidine loading (as shown in Table 9), as a result, also exhibits the highest chlorhexidine daily elution (as shown in Table 10 and FIG. 2). We are expecting much higher chlorhexidine daily elution with increased ionic content of such ionic compounds and increased chlorhexidine initial loading.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of manufacturing a medical device, the method comprising:
   incorporating an ionic additive into a base polymer to form an ionic compound; and
   ionically bonding the ionic compound and an active agent.

2. The method of claim 1, wherein the ionic additive is selected from an anionic additive, a cationic additive, and a zwitterionic additive.

3. The method of claim 1, wherein the base polymer is selected from a nonionic base polymer and an ionic base polymer.

4. The method of claim 2, wherein the anionic additive comprises a functional group selected from one or more of carboxylate ($—COO^-$), sulfonate ($—SO_3^-$), organosulfate

TABLE 10

| | SC-1-A Chlorhexidine Content ($\mu g/cm^2$) | SC-1-B Chlorhexidine Content ($\mu g/cm^2$) | SC-2-B Chlorhexidine Content ($\mu g/cm^2$) | SC-3-A Chlorhexidine Content ($\mu g/cm^2$) | SC-3-B Chlorhexidine Content ($\mu g/cm^2$) |
|---|---|---|---|---|---|
| Elution Medium | Human Serum | Human Serum | Bovine Serum | Bovine Serum | Bovine Serum |
| Elution 0-3 h | 11.8 | 16.0 | 50.9 | 3.5 | 34.9 |
| Elution 3-6 h | 3.4 | 6.8 | 12.3 | 0.9 | 7.6 |
| Elution 6-24 h | 3.9 | 12.5 | 40.3 | 2.2 | 17.3 |
| Elution 24-48 h | 2.7 | 7.0 | 18.3 | 2.0 | 7.0 |
| Elution 48-72 h | 2.4 | 4.9 | 10.0 | 0.9 | 2.6 |
| Elution 72-96 h | 2.5 | 4.1 | 7.3 | 0.2 | 1.1 |
| Elution 96-168 h | 2.6 | 4.9 | 7.6 | 0.8 | 1.3 |
| Remain | 124.9 | 238.9 | 410.1 | 238.2 | 233.2 |

(—O—SO$_3$$^-$), organophosphate (—O—PO$_3$$^-$R$^1$ or —O—PO$_3$$^{2-}$), phenolate (—C$_6$H$_4$—O$^-$), and thiolate (—S$^-$), wherein R$^1$ comprises hydrogen, halogen, alkyl, and aryl.

5. The method of claim 2, wherein the cationic additive comprises a functional group selected from one or more of quaternary ammonium (—N$^+$(R$^1$)(R$^2$)(R$^3$)), phosphonium (—P$^+$(R$^1$) (R$^2$) (R$^3$)), imidazolium, pyridinium, sulfonium, guanidinium, thiazolium, and quinolinium, wherein R$^1$, R$^2$, and R$^3$ independently comprise hydrogen, halogen, alkyl, and aryl.

6. The method of claim 2, wherein the zwitterionic additive comprises two or more functional groups selected from carboxylate (—COO$^-$), sulfonate (—SO$_3$$^{31}$), organosulfate (—O—SO$_3$$^-$), organophosphate (—O—PO$_3$$^-$R$^1$ or —O—PO$_3$$^{2-}$), phenolate (—C$_6$H$_4$—O$^-$), thiolate (—S$^-$), quaternary ammonium (—N$^+$(R$^1$)(R$^2$)(R$^3$)), phosphonium (—P$^+$(R$^1$)(R$^2$)(R$^3$)), imidazolium, pyridinium, sulfonium, guanidinium, thiazolium, and quinolinium, wherein R$^1$, R$^2$, and R$^3$ independently comprise hydrogen, halogen, alkyl, and aryl.

7. The method of claim 1, further comprising coating the ionically bonded ionic compound and the active agent on a body of the medical device.

8. The method of claim 1, further comprising compounding the ionically bonded ionic compound and the active agent to form a compounded mixture.

9. The method of claim 1, wherein a body of the medical device comprises the ionic compound ionically bonded to the active agent, and ionically bonding comprises imbibing the body of the medical device with the active agent.

10. The method of claim 1, wherein ionically bonding comprises preparing a formulation comprising the ionic compound and the active agent.

11. The method of claim 10, further comprising:
optionally, pre-swelling a body of the medical device;
optionally, deionizing the ionic compound; and
molding and/or extruding the formulation into the medical device.

12. The method of claim 1, wherein the active agent comprises one or more of an anionic active agent and a cationic active agent.

13. The method of claim 1, wherein the active agent is released over a span of at least 24 hours.

14. The method of claim 1, wherein the active agent is released over a span of at least three days.

15. The method of claim 1, wherein the active agent is released over a span of at least seven days.

16. The method of claim 1, wherein the active agent is released over a span of at least thirty days.

17. The method of claim 1, wherein the active agent is selected from the group consisting of an antimicrobial agent, an antithrombotic agent, or combinations thereof.

18. The method of claim 12, wherein the cationic active agent comprises one or more of chlorhexidine acetate, chlorhexidine gluconate, silver sulfadiazine, benzalkonium chloride, cetylpyridinium chloride, a quaternary ammonium-containing biocide, a guanidine-containing biocide, a cationic antimicrobial polymer, an antimicrobial peptide or peptide-mimics, an antifouling phospholipid or phospholipid-mimics, and derivatives thereof.

19. The method of claim 12, wherein the anionic active agent comprises one or more of cloxacillin salt, cefoxitin salt, cefazolin salt, penicillin salt, heparin salt, and derivatives thereof.

20. The method of claim 1, wherein the medical device is molded and/or extruded by injection molding and/or extrusion.

21. The method of claim 1, wherein the medical device is in the form of a catheter, an extension, an IV tubing, a catheter adapter, a luer port, a connector body, a device housing, a component thereof, or a combination thereof.

22. The method of claim 1, further comprising adding at least one excipient.

23. The method of claim 22, wherein the at least one excipient is selected from the group consisting of thermal stabilizers, light stabilizers, anti-blocking agents, antioxidants, antistatic agents, impact modifiers, reinforcing agents, flame retardants, mold release agents, blowing agents, colorants, and radiopaque fillers.

24. A method of manufacturing a medical device, the method comprising:
incorporating an ionic additive into a base polymer to form an ionic compound; and
ionically bonding the ionic compound and an active agent,
wherein a body of the medical device comprises the ionic compound ionically bonded to the active agent.

* * * * *